United States Patent

Angermann et al.

[11] Patent Number: 4,943,310
[45] Date of Patent: Jul. 24, 1990

[54] CYCLOHEXENECARBOXYLIC ACID DERIVATIVES AS PLANT GROWTH REGULANTS

[75] Inventors: Alfred Angermann; Helga Franke; Gerhard Johann, all of Berlin, Fed. Rep. of Germany

[73] Assignee: Schering Aktiengesellschaft, Fed. Rep. of Germany

[21] Appl. No.: 285,821

[22] Filed: Dec. 16, 1988

[30] Foreign Application Priority Data

Dec. 18, 1987 [DE] Fed. Rep. of Germany ....... 3743695

[51] Int. Cl.⁵ ................... A01N 43/00; C07C 87/30; C07D 265/32
[52] U.S. Cl. ........................ 71/88; 562/426; 562/429; 562/452; 562/460; 564/167; 564/169; 71/95; 71/94; 71/98; 71/103; 71/105; 71/107; 71/115; 71/118; 544/87; 544/163; 544/173; 546/173; 546/189; 546/226; 546/239; 548/517; 548/539; 560/45; 560/52; 560/11; 560/18
[58] Field of Search ................ 71/88, 95, 94, 98, 103, 71/105, 107, 115, 118; 260/501.5, 501.15; 544/87, 163, 173; 546/189, 226, 239; 548/517, 539; 556/49, 132; 560/45, 52, 11, 18; 562/426, 429, 452, 460; 564/167, 169

[56] References Cited

FOREIGN PATENT DOCUMENTS 0137963 4/1985 European Pat. Off. .

*Primary Examiner*—Anton H. Sutto
*Assistant Examiner*—C. L. Cseh
*Attorney, Agent, or Firm*—Ostrolenk, Faber, Gerb & Soffen

[57] ABSTRACT

The invention relates to new 4-benzoyl-3-hydroxy-5-oxo-3-cyclohexenecarboxylic acid derivatives of general formula I

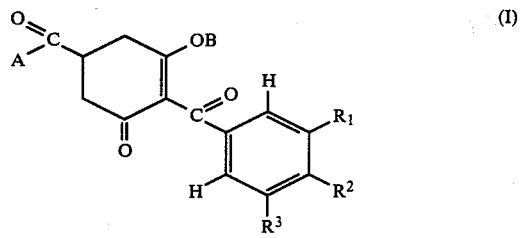

in which A, B, $R^1$, $R^2$, $R^2$ and $R^3$ have the meanings given in the description, and their use as plant growth regulants.

15 Claims, No Drawings

CYCLOHEXENECARBOXYLIC ACID DERIVATIVES AS PLANT GROWTH REGULANTS

DESCRIPTION

This invention relates to new 4-benzoyl-3-hydroxy-5-oxo-3-cyclohexenecarboxylic acid derivatives, processes for their preparation and their use as plant growth regulants.

It is known that certain cyclohexanedionecarboxylic acid derivatives possess herbicidal activity (EP applications 0 137 963 and 0 186 117). However until now, plant growth regulatory activity of these known compounds has not been observed.

The object of the present invention is to make new compounds that have improved biological properties over the known compounds.

The object is solved by new 4-benzoyl-3-hydroxy-5-oxo-3-cyclohexenecarboxylic acid derivatives of general formula I

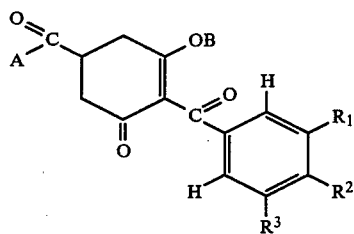

(I)

in which

A is $OR^4$, $NR^5R^6$ or $OM$,

B is hydrogen or a cation of the type M,

M is a cation from the group of lithium, sodium and potassium, an equivalent of zinc, manganese calcium, magnesium or barium or an ammonium ion of the general formula

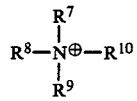

$R^1$, $R^2$ and $R^3$ independently of one another are hydrogen, halogen, hydroxy, cyano or nitro, or a $C_1$-$C_6$-alkyl, $C_2$-$C_6$-alkenyl, $C_2$-$C_6$-alkynyl, $C_1$-$C_{10}$-alkoxy, phenyl or benzyl group, which groups are optionally substituted by one or more of the same or different halogen, hydroxy, halo-$C_1$-$C_4$-alkyl, $C_1$-$C_4$-alkoxy, halo-$C_1$-$C_4$-alkoxy, $C_1$-$C_4$-alkylthio, $C_1$-$C_4$-alkylsulphinyl or $C_1$-$C_4$-alkylsulphonyl, or are $C_1$-$C_{10}$-alkylthio, $C_1$-$C_{10}$-alkylsulphinyl or $C_1$-$C_4$-alkylsulphonyl, or are one of the groups —$(CH_2)_nCOA$, —$(CH_2)_nCOR^4$ or —$NR^5R^6$, or $R^1$ and $R^2$ together are methylenedioxy, isopropylidenedioxy or ethylenedioxy, n is 0, 1 or 2, $R^4$ is hydrogen, or a $C_1$-$C_{18}$-alkyl, $C_2$-$C_{12}$-alkenyl, $C_2$-$C_{12}$-alkynyl group, which groups are optionally substituted by halogen or cyano or optionally interrupted one or more times by oxygen or sulphur, a $C_3$-$C_6$-cycloalkyl or $C_3$-$C_6$-cycloalkyl-$C_1$-$C_2$-alkyl group, which groups are optionally substituted by halogen or cyano, a phenyl or benzyl group, which groups are optionally substituted, one or more times, by halogen, cyano, $C_1$-$C_4$-alkyl, $C_1$-$C_4$-alkoxy, $C_1$-$C_4$-alkylthio, nitro or trifluoromethyl, or is a 5 or 6-membered heterocyclic group, $R^5$ and $R^6$ are the same or different and are hydrogen, or a $C_1$-$C_{18}$-alkyl, $C_2$-$C_{12}$-alkenyl, $C_2$-$C_{12}$-alkynyl group, which groups are optionally substituted by halogen or cyano or optionally interrupted one or more times by oxygen or sulphur, a phenyl or benzyl group, which groups are optionally substituted, one or more times, by $C_1$-$C_6$-alkyl, halogen, $C_1$-$C_6$-alkoxy or nitro, or $R^5$ and $R^6$ together with the adjacent nitrogen atom form a morpholino, piperidino or pyrrolidino group, and $R^7$, $R^8$, $R^9$ and $R^{10}$ are the same or different and are hydrogen, or a $C_1$-$C_6$-alkyl, phenyl, benzyl or phenylethyl group, which groups are optionally substituted by halogen, hydroxy or $C_1$-$C_6$-alkoxy.

The expression "halogen" means fluorine, chlorine, bromine and iodine. It is to be understood that the term "alkyl", "alkenyl" and "alkynyl" includes branched as well as straight chained hydrocarbon groups. Examples of 5 and 6-membered heterocyclic rings are furan, pyran, pyrrole, pyrrolidine, pyridine, piperidine, pyrazolidine, pyrimidine, oxazolidine, oxazole, morpholine, thiazole, thiazolidine and thiophene.

The compounds of the invention can exist also as tautomers. Thus 4-benzoyl-3-hydroxy-5-oxo-3-cyclohexenecarboxylic acid derivatives of general formula I, for example, can be represented also as the 3,5-dioxo structures of general formulae I' and I"

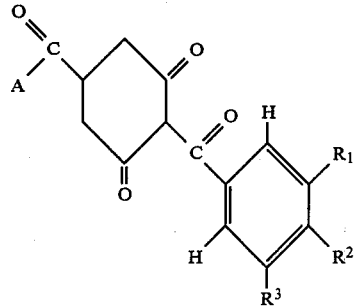

(I')

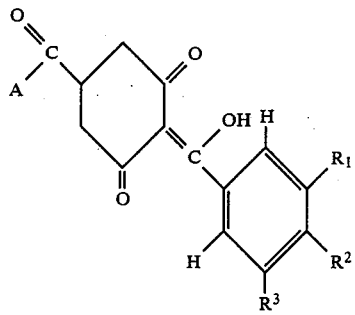

(I")

in which A, $R^1$, $R^2$ and $R^3$ have the meanings given under general formula I. These structures are also within the scope of the invention but for the sake of simplicity only the structures of general formula I are indicated.

The compounds of the invention of general formula I can be prepared for example by (A) subjecting a compound of general formula II

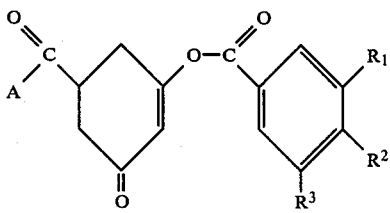

in which A, $R^1$, $R^2$ and $R^3$, to a catalytic rearrangement, or (B) reacting a compound of general formula III

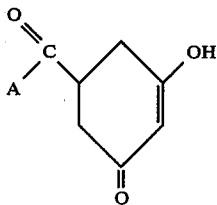

in which A has the meaning given under general formula I, with a benzoyl cyanide of general formula IV

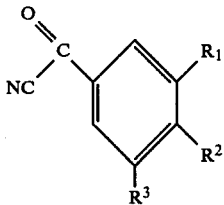

in which $R^1$, $R^2$ and $R^3$ have the meanings given under general formula I, in the presence of a Lewis acid and a suitable base, or (C) reacting a compound of general formula Ia

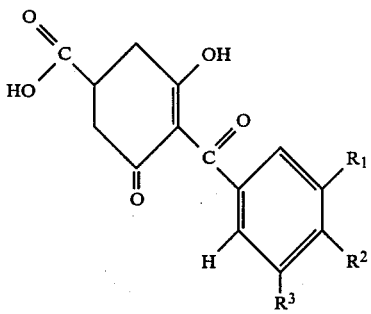

in which $R^1$, $R^2$ and $R^3$ have the meanings given under general formula I, with an alcohol or amine of general formula V or VI $R^4OH$  (V)

$HNR^5R^6$ TM (VI)

in which $R^4$, $R^5$ and $R^6$ have the meanings given under general formula I.

Suitable catalysts for the rearrangement reaction (A) include pyridine derivatives, such as for example 4-(N,N-dialkylamino)pyridine, preferably 4-(N,N-dimethylamino)pyridine, N-alkylimidazoles, such as for example N-methylimidazole, metal cyanides, such as for example copper(I)cyanide, sodium cyanide, potassium cyanide and zinc cyanide, 2-hydroxyisobutyronitrile or Lewis acids, such as for example zinc chloride or aluminum chloride.

The rearrangement reaction (A) is generally carried out in the presence of an inert solvent. Particularly suitable for this are aromatic hydrocarbons, such as benzene, toluene or xylene, halogenated hydrocarbons, such as for example carbon tetrachloride, chloroform or dichloromethane, acetonitrile or organic bases, such as triethylamine and pyridine.

The starting materials of general formula II can be obtained by acylation of a cyclohexenecarboxylic acid derivative of general formula III

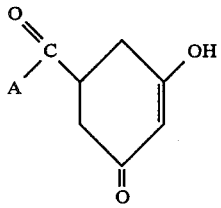

in which A has the meaning given in general formula I, with benzoyl halide of general formula VII

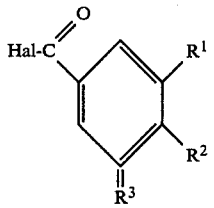

in which $R^1$, $R^2$ and $R^3$ have the meanings given under general formula I and Hal is a halogen atom, preferably chlorine or bromine.

This reaction can optionally be carried out in the presence of an inert solvent and an acid binding agent. Suitable binding agents include various organic and inorganic bases and especially triethylamine or pyridine.

The preparation variant (B) is generally a one-pot process. The reaction can be suitable carried out by mixing the benzoyl cyanide of general formula IV, the compound of general formula II and the Lewis acid at room temperature in an inert solvent and adding dropwise a base to this mixture at room temperature or below.

The solvents used for preparation variant (B) are suitable for this reaction.

Preferred Lewis acids are zinc and/or aluminium chloride or bromide. Suitable bases are tertiary amines, such as for example triethylamine or pyridine.

Preparation variant (C) can be carried out using standard esterification and/or amidation methods. In this case it is especially advantageous to carry out the azeotropic esterification in benzene or toluene in the presence of p-toluenesulphonic acid or phosphoric acid. It is particularly suitable in this process if a water separation is achieved for example by treatment of the components with thionyl chloride, oxalyl chloride, dicyclohexylcarbodiimide or a triphenylphosphane/alkyl azodicarboxylate system.

Solvents which can be used in preparation variants (A), (B) and (C), besides those which have already been mentioned, are any solvents which are inert to the reactants. Examples of such solvents or diluents are aliphatic, alicyclic and aromatic hydrocarbons each of which can be optionally chlorinated, such as for example hexane, cyclohexane, petroleum ether, naphtha, benzene, toluene, methylene chloride, chloroform, carbon tetrachloride, ethylene dichloride, trichloroethane and chlorobenzene, ethers, such as for example diethyl ether, methyl ethyl ether, methyl t-butyl ether, diisopropyl ether, dibutyl ether, dioxane and tetrahydrofuran, ketones such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphoxides, such as for example dimethyl sulphoxide and and sulpholane, and bases, such as for example pyridine.

The reaction variants (A), (B) and (C) are preferably carried out at atmospheric pressure, although higher or lower pressures can be used. They can also be carried out over a wide temperature range. In general a temperature of between $-20°$ C. and the boiling point of the reaction mixture, preferably $0°-150°$ C. is used.

In the preparation methods (A), (B) and (C), the presence of additional reaction catalysts can be an advantage. Such catalysts include potassium iodide and onium compounds, such as quarternary ammonium, phosphonium, arsonium and sulphonium compounds. Also suitable are polyglycol ethers especially cyclic ethers, such as for example 18-crown-6. and tertiary amines, such as for example tributylamine. Especially suitable are quaternary ammonium compounds, such as for example benzyl triethylammonium bromide and tetrabutylammonium bromide.

The compounds of the invention are, as a rule, colourless or odourless liquids or crystals that are slightly soluble in water and in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, sulphoxides, such as dimethyl sulphoxide, and bases, such as pyridine. Because of there acidic character the compounds of the invention are also soluble in aqueous carbonate, hydrogen carbonate and hydroxide solutions.

The compounds of the invention, as well as causing qualitative and quantitative changes in plants, also cause changes in the metabolism of plants and are therefore classed as plant growth regulants which can be distinguished by the following use possibilities:

Arresting the vegetative growth in woody and vegetative plants, for example at roadsides, railways and other places, in order to stop luxuriant growth. Arresting of growth in cereals in order to stop lodging or bending, and in cotton for increase of productivity.

Influencing the branching of vegetative and generative parts in ornamental and cultivated plants to increase flowering or in tobacco and tomatoes to inhibit sideshoots.

Improving the quality of fruit for example by increasing the sugar content in sugar cane, sugar beet or in fruits and a similar ripening of harvested goods which leads to higher yields.

Increasing the resistance to stress both for example against climatic influences, such as cold and dryness, and also against phytotoxic influences of chemicals.

Influencing the latex flow of rubber plants.

Formation of parthenocarpic fruits, pollen sterility and sexual influences are also use possibilities.

Control of the germination of seeds or separation of buds.

Defoliation or influencing fruit fall for easier harvesting.

The compounds of the invention are especially suitable for the inhibition of vegetative growth in various plant types. Such growth inhibition has been produced up until now in the art with substances which either do not work consistently or whose activity is more variable than the compounds of the invention.

Besides this there is for example substances for various cereal types which can be treated in order to shorten the stalks and to give the plants a greater rigidity. In addition with such an activity, growing plants can be inhibited where growth in certain places is not desirable, such as for example on road verges, railway sidings or airports. Also, lawns can be treated so that less cutting is necessary. Growth regulant effects are achieved with such substances in general also in crops in which the removal of quiescent branches is to be intensively avoided, such as for example tobacco.

In cotton, growth regulation can lead to a similar ripening of the capsules thus to higher yields.

In fruit trees, the influence in vegetative growth can lead to increases in yield and economic advantages.

In ornamental plants, a growth reduction is often achieved that can lead to more plants per pot.

Compounds of the invention can be applied pre and post emergently. The rates of use depending on the desired use are from 0.001 to 5 kg/ha, although higher amounts can be used. The timing depends on the target and the climatic conditions.

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrogenated phosphatidylcholines phosphatidylethanolamine, N-acyl-phosphatidyl-ethanolamines, phosphatidylinositol, phosphatidylserine, lysolecithin or phosphatidylglycerol.

The designated active ingredients or their mixtures can suitable be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ethers, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

The following examples illustrate the preparation of compounds according to the invention.

EXAMPLE 1

Ethyl 4-benzoyl-3-hydroxy-5-oxo-3-cyclohexenecarboxylate 7.75 g (55.1 mmol) Benzoyl chloride was added dropwise to 10.00 g (54.3 mmol) ethyl 3,5-dioxocyclohexanecarboxylate, dissolved in 100 ml dichloromethane and 15 ml triethylamine, at 10° C. The mixture was stirred for 3 hours at room temperature, poured into ice, separated, the organic phase shaken with 1N hydrochloric acid, saturated sodium bicarbonate and water, dried (magnesium sulphate) and concentrated. The ethyl 3-benzoyloxy-5-oxo-3-cyclohexenecarboxylate, so obtained, was dissolved in 75 ml acetonitrile and after addition of 15 ml triethylamine and 1.5 ml 2-hydroxyisobutyronitrile, was stirred at 24 hours at room temperature. The mixture was taken up in 100 ml diethyl ether and extracted with 100 ml 2N hydrochloric acid and then twice with, each time, 50 ml 5% potassium carbonate solution. After covering the aqueous phase with a layer of 100 ml diethyl ether, it was acidified with 4N hydrochloric acid until it was pH 3, separated, washed with water, dried (magnesium sulphate) and evaporated on a rotary evaporator. It was purified by recrystallising from hexane.

Yield: 8.8 g=56.3% of theory
mp: 58°–60° C.

Elementary analysis: Calculated: C 66.66%; H 5.59%. Found: C 66.64%; H 5.34%.

EXAMPLE 2

Ethyl 4-(3,4 dichlorobenzoyl)-3-hydroxy-5-oxo-3-cyclohenecarboxylate 6.1 g (4.48 mmol) Anhydrous zinc chloride was added to a solution of 8.00 g (43.4 mmol) ethyl 3,5-dioxocyclohexane carboxylate and 8.90 g (44.5 mmol) 3,4-dichlorobenzoyl cyanide in 150 ml dichloromethane. To this mixture, 4.80 g (47.4 mmol) triethylamine was added, dropwise, at 0° C. over 30 minutes. The mixture was stirred for 14 hours at room temperature and worked up as in Example 1. The residue was purified by column chromotography (hexane/ethyl acetate, v/v 80:20) on silica gel to give the desired product.

Yield: 8.2 g=52.8% of theory
mp: 73°–74° C.

Elementary Analysis Calculated: C 53.80%; H 3.95%; Cl 19.85%. Found: C 54.02%; H 3.91%; Cl 20.13%.

In a similar manner to Examples 1 or 2, the following compounds were prepared.

| Example | Name of compound | Physical Constant mp (°C.)/$n_D^{20}$ |
|---|---|---|
| 3 | ethyl 4-(3-methylbenzoyl)-3-hydroxy-5-oxo-3-cyclohexenecarboxylate | 38 |
| 4 | ethyl 4-(4-methylbenzoyl)-3-hydroxy-5-oxo-3-cyclohexenecarboxylate | 1.5742 |
| 5 | ethyl 4-(4-n-propylbenzoyl)-3-hydroxy-5-oxo-3-cyclohexenecarboxylate | 60 |
| 6 | ethyl 4-(4-n-butylbenzoyl)-3-hydroxy-5-oxo-3-cyclohexenecarboxylate | 44 |
| 7 | ethyl 4-(4-t-butylbenzoyl)-3-hydroxy-5-oxo-3-cyclohexenecarboxylate | 1.5604 |
| 8 | ethyl 4-(3-chlorobenzoyl)-3-hydroxy-5-oxo-3-cyclohexenecarboxylate | 1.5758 |
| 9 | ethyl 4-(4-chlorobenzoyl)-3-hydroxy-5-oxo-3-cyclohexenecarboxylate | 53 |
| 10 | ethyl 4-(3-fluorobenzoyl)-3-hydroxy-5-oxo-3-cyclohexenecarboxylate | 1.5586 |
| 11 | ethyl 4-(4-bromobenzoyl)-3-hydroxy-5-oxo-3-cyclohexenecarboxylate | 83.5–84 |
| 12 | ethyl 4-(3-nitrobenzoyl)-3-hydroxy-5-oxo-3-cyclohexenecarboxylate | 1.5778 |
| 13 | ethyl 4-(3-methoxybenzoyl)-3-hydroxy-5-oxo-3-cyclohexenecarboxylate | 54 |
| 14 | ethyl 4-(4-methoxybenzoyl)-3-hydoxy-5-oxo-3-cyclohexenecarboxylate | 101–102 |
| 15 | ethyl 4-(4-n-butoxybenzoyl)-3-hydroxy-5-oxo-3-cyclohexenecarboxylate | 49 |
| 16 | ethyl 4-(3,4-dimethylbenzoyl)-3-hydroxy-5-oxo-3-cyclohexenecarboxylate | 37 |
| 17 | ethyl 4-(3,5-dimethylbenzoyl)-3-hydroxy-5-oxo-3-cyclohexenecarboxylate | 1.5663 |
| 18 | ethyl 4-(3,5-dichlorobenzoyl)-3-hydroxy-5-oxo-3-cyclohexenecarboxylate | 34 |
| 19 | ethyl 4-(3-trifluoromethylbenzoyl)-3-hydroxy-5-oxo-3-cyclohexenecarboxylate | 45–46 |
| 20 | 4-(3-chlorobenzoyl)-3-hydroxy-5-oxo-3-cyclohexenecarboxylic acid, monohydrate | 84 |
| 21 | 4-(3-chlorobenzoyl)-3-hydroxy-5-oxo-3-cyclohexenecarboxylic acid | 181 |
| 22 | 4-(3,4-dichlorobenzoyl)-3-hydroxy-5-oxo-3-cyclohexenecarboxylic acid, monohydrate | 111–127 |
| 23 | sodium salt of ethyl 4-(3-chlorobenzoyl)-3-hydroxy-5-oxo-3-cyclohexenecarboxylate | 277 |
| 24 | sodium salt of ethyl 4-(4-chlorobenzoyl)-3-hydroxy-5-oxo-3-cyclohexenecarboxylate | 303 |
| 25 | sodium salt of ethyl 4-(3,4-dichlorobenzoyl)-3-hydroxy-5-oxo-3-cyclohexenecarboxylate | |
| 26 | sodium salt of ethyl 4-(3-methoxybenzoyl)-3-hydroxy-5-oxo-3-cyclohexenecarboxylate | 197 |
| 27 | sodium salt of ethyl 4-(3-fluorobenzoyl)-3-hydroxy-5-oxo-3-cyclohexenecarboxylate | 268 |
| 28 | sodium salt of ethyl 4-(4-fluorobenzoyl)-3-hydroxy-5-oxo-3-cyclohexenecarboxylate | 281 |
| 29 | sodium salt of ethyl 4-benzoyl-3-hydroxy-5-oxo-3-cyclohexenecarboxylate | 252–254 |
| 30 | ethyl 4-(4-ethylbenzoyl)-3-hydroxy-5-oxo-3-cyclohexenecarboxylate | 56 |
| 31 | ethyl 3-hydroxy-4-(4-nitrobenzoyl)-5-oxo-3-cyclohexenecarboxylate | 51–53 |

-continued

| Example | Name of compound | Physical Constant mp (°C.)/$n_D^{20}$ |
|---|---|---|
| 32 | 4-(3,5-dichlorobenzoyl)-3-hydroxy-5-oxo-3-cyclohexenecarboxylic acid | 172–173 |
| 33 | methyl 4-(4-chlorobenzoyl)-3-hydroxy-5-oxo-3-cyclohexenecarboxylate | 88–89 |
| 34 | methyl 3-hydroxy-4-(4-trifluoromethoxybenzoyl)-5-oxo-3-cyclohexenecarboxylate | 93–94 |
| 35 | ethyl 3-hydroxy-4-(4-trifluoromethoxybenzoyl)-5-oxo-3-cyclohexenecarboxylate | 78–79 |
| 36 | disodium 4-(3,4-dichlorobenzoyl)3-hydroxy-5-oxo-3-cyclohexenecarboxylate | 292 |
| 37 | ethyl 4-(4-difluoromethoxybenzoyl)-3-hydroxy-5-oxo-3-cyclohexenecarboxylate | 78–80 |
| 38 | methyl 4-(4-difluoromethoxybenzoyl)-3-hydroxy-5-oxo-3-cyclohexenecarboxylate | 92–95 |
| 39 | methyl 3-hydroxy-4-(4-methylsulphonyl-benzoyl)-5-oxo-3-cyclohexenecarboxylate | 137–139 |
| 40 | ethyl 3-hydroxy-4-(4-methylsulphonyl-benzoyl)-5-oxo-3-cyclohexenecarboxylate | 105 |
| 41 | ethyl 3-hydroxy-4-(4-methylthio-benzoyl)-5-oxo-3-cyclohexenecarboxylate | 93–94 |
| 42 | methyl 3-hydroxy-4-(4-methylthio-benzoyl)-5-oxo-3-cyclohexenecarboxylate | 108–109 |
| 43 | methyl 4-(4-ethylthiobenzoyl)-3-hydroxy-5-oxo-3-cyclohexenecarboxylate | 69–71 |
| 44 | ethyl 4-(4-ethylthiobenzoyl)-3-hydroxy-5-oxo-3-cyclohexenecarboxylate | 70–71 |

The following examples illustrate the possibilities for use of the compounds of the invention.

EXAMPLE A

Growth inhibition activity in rice and barley

Rice and barley were grown in humus rich earth up to the two-leaf stage. The plants were sprayed with active ingredients at a rate of 0.5–1 kg/ha. Fourteen days after the treatment the length of the stalk above the earth up to the onset of the first fully developed leaf was measured. The data so obtained were compared with a control and the growth inhibition activity evaluated according to the following scheme:

0 = ≧91% of the growth height in the untreated control
1 = 81–90% of the growth height in the untreated control
2 = 71–80% of the growth height in the untreated control
3 = 61–70% of the growth height in the untreated control
4 = ≦60% of the growth height in the untreated control

| Compound of the invention | Rate of application (kg/ha) | Growth inhibition activity Barley | Rice |
|---|---|---|---|
| Example 1 | 0.5 | 2 | 3 |
| | 1.0 | 3 | 4 |
| Example 4 | 0.5 | 4 | 2 |
| | 1.0 | 4 | 2 |
| Example 9 | 0.5 | 2 | 2 |
| | 1.0 | 4 | 4 |
| Example 10 | 0.5 | 2 | 3 |
| | 1.0 | 2 | 3 |
| Example 11 | 0.5 | 3 | 0 |
| | 1.0 | 4 | 2 |
| Example 14 | 0.5 | 2 | 1 |
| | 1.0 | 2 | 3 |
| Example 24 | 0.5 | 3 | 1 |
| | 1.0 | 4 | 1 |
| Example 33 | 0.5 | 3 | 1 |
| | 1.0 | 4 | 3 |

-continued

| Compound of the invention | Rate of application (kg/ha) | Growth inhibition activity Barley | Rice |
|---|---|---|---|
| Comparison (according to EP 137 963) | | | |
| 2-(2,4-Dichlorobenzoyl)-5,5-dimethyl-1-hydroxy-3-oxo-1-cyclohexene | 0.5 | 0 | 0 |
| | 1.0 | 0 | 0 |
| Comparison (commercial product) | | | |
| chlormequat chloride | 0.8 | 2 | 1 |

As the example shows, compounds of the same class and also the commercial standard had weaker activity than the compounds of the invention.

EXAMPLE B

Growth inhibition in paddy rice

Rice plants were grown in plastic pots up to the two to three-leaf stage and treated with the compounds of the invention and the application was carried out into the water. Eighteen days after the height of the plant up to the onset of the first fully developed leaf was measured. The data so obtained were compared with a control and the growth inhibition activity evaluated according to the following scheme:

0 = ≧91% of the growth height in the untreated control
1 = 81–90% of the growth height in the untreated control
2 = 71–80% of the growth height in the untreated control
3 = 61–70% of the growth height in the untreated control
4 = ≦60% of the growth height in the untreated control

| Compound of the invention | Rate of application (kg/ha) | Growth inhibition activity |
|---|---|---|
| Example 3 | 1.0 | 1 |
| | 3.0 | 3 |
| Example 8 | 1.0 | 3 |
| | 3.0 | 4 |
| Example 9 | 1.0 | 2 |
| | 3.0 | 2 |
| Example 10 | 1.0 | 3 |
| | 3.0 | 4 |
| Example 13 | 1.0 | 2 |
| | 3.0 | 4 |
| Example 14 | 1.0 | 3 |
| | 3.0 | 4 |
| Example 24 | 1.0 | 2 |
| | 3.0 | 4 |
| Example 27 | 1.0 | 2 |
| | 3.0 | 4 |
| Example 28 | 1.0 | 3 |
| | 3.0 | 4 |
| Example 30 | 1.0 | 2 |
| | 3.0 | 4 |
| Example 33 | 1.0 | 3 |
| | 3.0 | 3 |
| Example 38 | 1.0 | 4 |
| | 3.0 | 4 |

We claim:
1. 4-Benzoyl-3-hydroxy-5-oxo-3-cyclohexenecarboxylic acid derivative of formula I

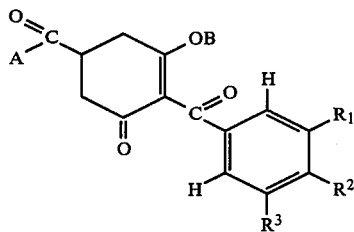

in which

A is OR[4] or OM,

B is hydrogen or a cation of the type M,

M is a cation from the group of lithium, sodium and potassium, $R^1$, $R^2$ and $R^3$ independently of one another are hydrogen, halogen, or nitro, or a $C_1$–$C_6$-alkyl or $C_1$–$C_{10}$-alkoxy group, which groups are optionally substituted by at least one halogen, sulphinyl or $C_1$–$C_4$-alkylsulphonyl, or are $C_1$–$C_{10}$-alkylthio, or $C_1$–$C_4$-alkylsulphonyl, $R^4$ is hydrogen or a $C_1$–$C_{18}$-alkyl group, which groups are optionally substituted by halogen or cyano or optionally interrupted one or more times by oxygen or sulphur, a $C_3$–$C_6$-cycloalkyl or $C_3$–$C_6$-cycloalkyl-$C_1$–$C_2$-alkyl group, which groups are optionally substituted by halogen or cyano, a phenyl or benzyl group, which groups are optionally substituted, one or more times, by halogen, cyano, $C_1$–$C_4$-alkyl, $C_1$–$C_4$-alkoxy, $C_1$–$C_4$-alkylthio, nitro or trifluoromethyl, or is a 5 or 6-membered heterocyclic group, $R^5$ and $R^6$ are the same or different and are hydrogen, or a $C_1$–$C_{18}$-alkyl, $C_2$–$C_{12}$-alkenyl, $C_2$–$C_{12}$-alkynyl group, which groups are optionally substituted by halogen or cyano or optionally interrupted one or more times by oxygen or sulphur, a phenyl or benzyl group, which groups are optionally substituted, one or more times, by $C_1$–$C_6$-alkyl, halogen, $C_1$–$C_6$-alkoxy or nitro, or $R^5$ and $R^6$ together with the adjacent nitrogen atom form a morpholino, piperidino or pyrrolidino group, and $R^7$, $R^8$, $R^9$ and $R^{10}$ are the same or different and are hydrogen, or a $C_1$–$C_6$-alkyl, phenyl, benzyl or phenylethyl group, which groups are optionally substituted by halogen, hydroxy or $C_1$–$C_6$-alkoxy.

2. A plant growth regulating composition which comprises an effective regulating amount of a compound according to claim 1, in admixture with carriers and diluents.

3. A method of regulating the growth of plants which comprises applying to the plants or their locus an effective regulating amount of a compound according to claim 1.

4. 4-Benzoyl-3-hydroxy-5-oxo-3-cyclohexenecarboxylic acid derivative according to claim 1 in which A is $OR^4$, $R^1$ is hydrogen or halogen, $R^2$ is hydrogen, halogen, $C_1$–$C_6$-alkyl, halo-$C_1$–$C_6$-alkyl or $C_1$–$C_{10}$-alkoxy, $R^3$ is hydrogen and $R^4$ is hydrogen or $C_1$–$C_{18}$-alkyl.

5. 4-Benzoyl-3-hydroxy-5-oxo-3-cyclohexenecarboxylic acid derivative according to claim 4 in which $R^1$ is hydrogen, $R^2$ is halogen and $R^4$ is alkyl.

6. 4-Benzoyl-3-hydroxy-5-oxo-3-cyclohexenecarboxylic acid derivative according to claim 5 in which B is hydrogen or sodium and $R^4$ is methyl or ethyl.

7. 4-Benzoyl-3-hydroxy-5-oxo-3-cyclohexenecarboxylic acid derivative according to claim 6 in which B is hydrogen, $R^2$ is chlorine and $R^4$ is ethyl.

8. A plant growth regulating composition which comprises an effective regulating amount of a compound according to claim 4, in admixture with carriers and diluents.

9. A plant growth regulating composition which comprises an effective regulating amount of a compound according to claim 5, in admixture with carriers and diluents.

10. A plant growth regulating composition which comprises an effective regulating amount of a compound according to claim 6, in admixture with carriers and diluents.

11. A plant growth regulating composition which comprises an effective regulating amount of a compound according to claim 7, in admixture with carriers and diluents.

12. A method of regulating the growth of plants which comprises applying to the plants or their locus an effective regulating amount of a compound according to claim 4.

13. A method of regulating the growth of plants which comprises applying to the plants or their locus an effective regulating amount of a compound according to claim 5.

14. A method of regulating the growth of plants which comprises applying to the plants or their locus an effective regulating amount of a compound according to claim 6.

15. A method of regulating the growth of plants which comprises applying to the plants or their locus an effective regulating amount of a compound according to claim 7.

* * * * *